United States Patent [19]

Tsuboshima

[11] 4,332,658
[45] Jun. 1, 1982

[54] CHEMICAL SUBSTANCE DETECTION APPARATUS

[75] Inventor: Kosaku Tsuboshima, Hachioji, Japan

[73] Assignee: Olympus Optical Company, Ltd., Tokyo, Japan

[21] Appl. No.: 184,058

[22] Filed: Aug. 28, 1980

[30] Foreign Application Priority Data

Sep. 10, 1979 [JP] Japan .................................. 54-115104

[51] Int. Cl.³ ....................... G01N 27/26; G01N 27/30
[52] U.S. Cl. ........................... 204/195 M; 204/195 R; 324/425; 357/25
[58] Field of Search ....................... 204/195 R, 195 M; 357/25; 324/425; 128/635

[56] References Cited

U.S. PATENT DOCUMENTS

| | | | |
|---|---|---|---|
| 3,709,796 | 1/1973 | King et al. ........................... | 204/1 T |
| 4,020,830 | 5/1977 | Johnson et al. ............. | 204/195 M X |
| 4,218,298 | 8/1980 | Shimada et al. ................ | 204/195 M |
| 4,267,504 | 5/1981 | Bergveld .......................... | 324/425 X |

Primary Examiner—G. L. Kaplan
Attorney, Agent, or Firm—Stevens, Davis, Miller & Mosher

[57] ABSTRACT

A chemical substance detection apparatus comprising a plurality of chemically sensitive elements constructed as an insulation gate field effect transistor formed on one or different substrates and including chemically sensitive portions selectively sensitive to different specified substances and one reference electrode, at least the chemically sensitive portions as well as the one reference electrode being brought into contact with the same test substance so as to detect various specified substances in the test substance, characterized by comprising reference resistors, first amplifiers operative to adjust gain thereof, a differential amplifier in common to all of said amplifiers and applying its output voltage to the reference electrode and a reference gate bias voltage source connected to the input terminals of the differential amplifier and supplying the reference gate bias voltage thereto.

6 Claims, 2 Drawing Figures

4,332,658

CHEMICAL SUBSTANCE DETECTION APPARATUS

BACKGROUND OF THE INVENTION

1. Field of the Invention

This invention relates to a chemical substance detection apparatus comprising a plurality of chemically sensitive elements constructed as an insulation gate field effect transistor formed on one or different substrates and including chemically sensitive portions selectively sensitive to different specified substances and one reference electrode, at least said chemically sensitive portions as well as said one reference electrode being brought into contact with the same test substance so as to detect various specified substances in said test substance.

2. Description of the Prior Art

Various chemically sensitive elements constructed as a field effect transistor provided at its gate portion with a chemically sensitive portion which is sensitive to a specified chemical substance and can detect various kinds of ions, gas, enzyme, antibodies or the like have heretofore been proposed. Such chemically sensitive element is composed of a chemically sensitive portion formed on one semiconductor substrate and operative to be selectively sensitive to one specified chemical substance or composed of a plurality of chemically sensitive portions formed on one semiconductor substrate and operative to be selectively sensitive to different chemical substances. Various methods of detecting a specified ion concentration and activity in a test liquid such as serum or the like by means of the above mentioned chemically sensitive element such, for example, as an ion sensor have also been proposed.

On the one hand, in biochemistry field, many items of ion concentrations and activities are often measured from the same test liquid in general. In this case, as one of the measuring methods, the same test liquid is injected into a plurality of containers and respective measuring circuits are constructed for these containers and the measurement is effected by means of a multi-channel system. But, in this method, the items of ion concentration and activity are measured independently, so that this method must use much amount of test liquid and is troublesome in operation. Particularly, if use is made of an ion sensor composed of a plurality of chemically sensitive portions formed on the same semiconductor substrate and sensitive to different ions, the ability of the ion sensor could not be fully revealed. Such drawback of the ion sensor has also been encountered with a gas sensor, enzyme sensor, immunity sensor or the like.

SUMMARY OF THE INVENTION

An object of the invention, therefore, is to provide a chemical substance detection apparatus which makes use of a chemically sensitive element constructed as an insulation gate field effect transistor, which can eliminate the above mentioned drawbacks which have been encountered with the prior art techniques and which can easily detect a number of terms of specified chemical substance in the same cell by using a small amount of test substance.

A feature of the invention is the provision in a chemical substance detection apparatus comprising a plurality of chemically sensitive elements constructed as an insulation gate field effect transistor formed on one or different substrates and including chemically sensitive portions selectively sensitive to different specified substances and one reference electrode, at least said chemically sensitive portions as well as said one reference electrode being brought into contact with the same test substance so as to detect various specified substances in said test substance, of the improvement comprising reference resistors connected to sources of said chemically sensitive elements, respectively, first amplifiers connected to said reference resistors, respectively, and supplied with the voltages produced across each of said reference resistors, said first amplifiers being operative to adjust gain thereof, a differential amplifier connected in common to said first amplifiers and having two input terminals one of which is selectively applied with the output voltage of said first amplifiers, said differential amplifier applying its output voltage to said reference electrode, and a reference gate bias voltage source connected to the other input terminal of said differential amplifier and supplying the reference gate bias voltage thereto, whereby said bias voltage applied to said reference electrode is selectively controlled such that a given current always flows the drain source path of each of said chemically sensitive elements and various specified substances in said test substance are selectively detected on the basis of the bias voltage value.

Further objects and features of the invention will be fully understood from the following detailed description with reference to the accompanying drawings, wherein:

DETAILED DESCRIPTION OF THE PREFERRED EMBODIMENT

Figure 1:
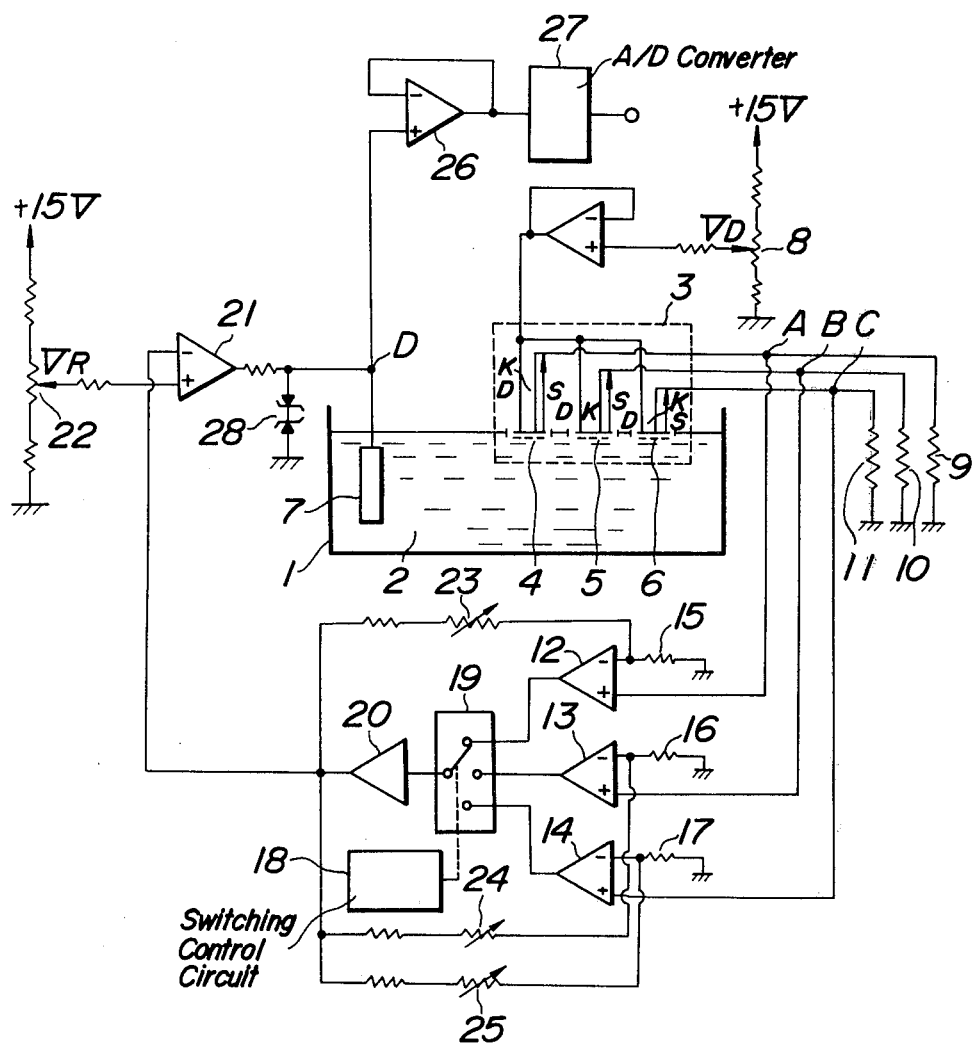
FIG. 1 is a diagrammatic view showing one embodiment of a chemical substance detection apparatus according to the invention.

FIG. 1 shows one embodiment of a chemical substance detection apparatus according to the invention. In the present embodiment, the chemical substance detection apparatus is operative to measure three items of ion concentration and activity of a test liquid 2 contained in a container 1. In the present embodiment, provision is made of an ion sensor 3 which is constructed as an insulation gate field effect transistor formed on the same semiconductor substrate and selectively sensitive to desirous three different kinds of ions. The ion sensor 3 is provided with ion sensitive portions 4, 5 and 6 which are brought into contact with the test liquid 2 into which is immersed a reference electrode 7. Each ion sensor including the ion sensitive portion is composed of a drain terminal D, source terminal S and semiconductor substrate K. The drain terminals D are connected to a common electric supply source 8 and applied with a constant direct current voltage $V_D$, whereas all of the source terminals S and semiconductor substrates K are connected through reference resistors 9, 10, 11 to ground. Joint connections A, B, C between the ion sensitive portions and the reference resistors 9, 10, 11 are connected to one of input terminals of first amplifiers 12, 13, 14, respectively, so as to apply the voltages at the junction points A, B, C to one of the input terminals of the first amplifiers 12, 12, 14, respectively, the other input terminals of these amplifiers 12, 13, 14 being connected through resistors 15, 16, 17 to ground, respectively. The output voltages from the first amplifiers 12, 13, 14 are selectively supplied through an analog switch 19 driven by a switching control circuit 18 and a second amplifier 20 to one of input terminals of a differential amplifier 21. To the other input terminal of the differential amplifier 21 is supplied a constant reference bias voltage $V_R$ from a bias electric voltage source 22. Between the output terminal of the second amplifier 20 and the negative input terminals of the first amplifiers 12, 13, 14 are connected feed back paths including variable resistors 23, 24, 25 so as to adjust gain of these amplifiers, respectively.

The output terminal of the differential amplifier 21 is connected to the reference electrode 7. The voltage $V_x$ produced at this output terminal is detected by an amplifier 26 whose output is supplied to a A/D converter 27 to obtain a digital value which is digitally displayed. In addition, the output terminal of the differential amplifier 21 is connected through a Zener diode 28 to ground, thereby preventing the reference electrode 7 from being applied with an abnormally high voltage and hence preventing the semiconductor ion sensor 3 from being damaged.

In the present invention, in order to improve the ion measuring accuracy, each element of the semiconductor ion sensor 3 is made operative at a constant current. That is, each element of the semiconductor ion sensor 3 is operated such that the drain-source current of each element always takes a constant value.

Figure 2:
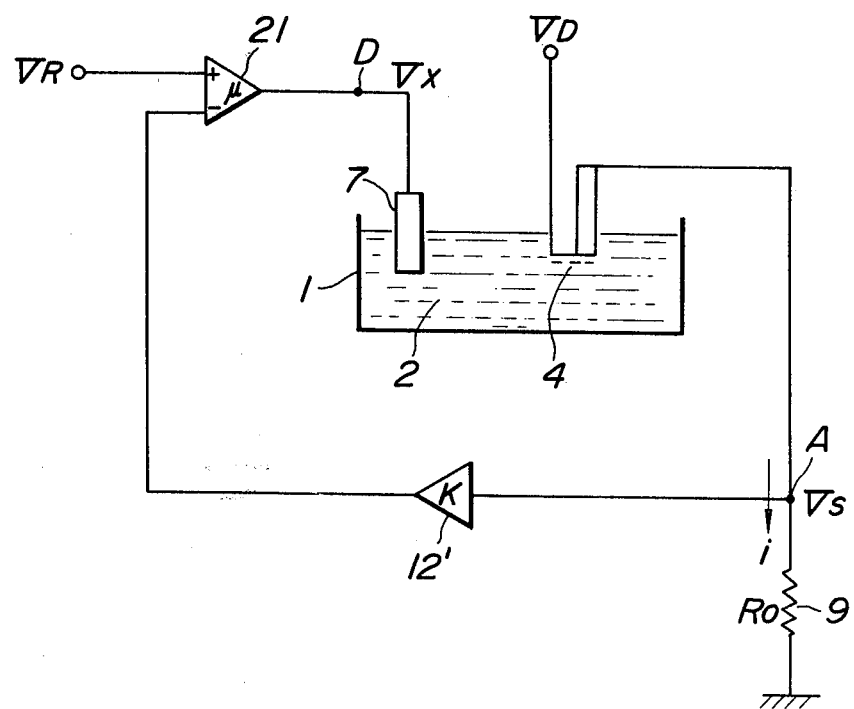
FIG. 2 is a diagrammatic view for illustrating the operation of one measuring channel shown in FIG. 1.

FIG. 2 shows one measuring channel associated with one chemically sensitive element of the circuit shown in FIG. 1. One amplifier 12' shown in FIG. 2 represents the first amplifier 12, analog switch 19 and second amplifier 20 shown in FIG. 1. Now, let it be assumed that the resistance value of the resistor 9 be $R_0$, gain of the amplifier 12' be K, gain of the differential amplifier $\mu$, voltage at the output terminal of the differential amplifier 21, that is, the voltage at the point D applied to the reference electrode 7 be $V_x$ and drain-source current of the ion sensor element be i. In the present invention, the values of $R_0$, K, $\mu$ and $V_R$ are selected such that the drain-source current i takes a given value when the ion sensor is immersed into a test liquid containing given ion having a certain concentration. Let the drain-source current be $i_0$, then the potential $V_{x0}$ at the reference electrode 7 is given by $$V_{x0} = (V_R - K i_0 R_0)\mu.$$

Under such condition, if the ion concentration is increased, for example, and the drain-source current is increased to $i_0 + \Delta i$, the potential $V_x$ at the reference electrode 7 is given by $$V_x = (V_R - K(i_0 + \Delta i) R_0)\mu$$
$$= V_{x0} - \mu K \Delta i R_0$$

That is, $V_x$ is decreased from $V_{x0}$ by $\mu K \Delta i R_0$. As a result, the drain-source current is decreased to $i_0$ and becomes stable under such condition. In this case, $V_x$ is decreased from $V_{x0}$ by a voltage component induced by the ion in the gate region. As a result, if the decreased portion from the voltage $V_x$ is measured, it is possible to measure the increased portion of the ion concentration. On the contrary, if the drain-source current is decreased to a value smaller than $i_0$, the voltage $V_x$ becomes increased to a value which can compensate the decreased portion. In this way, it is possible to know change in the ion concentration by detecting increased portion or decreased portion of the voltage $V_x$ to be applied to the reference voltage 7.

In addition, the chemical substance detection apparatus according to the invention is capable of measuring many kinds of ion concentrations, for example, three kinds of ion concentrations of the test liquid 2. Concerning each measuring channel, the potential $V_x$ at the point D changes such that the drain-source current of each element always takes a constant value, as described above with reference to FIG. 2. If the analog switch 19 is changed over in succession by means of the switching control circuit 18, the voltages corresponding to the points A, B and C are applied to the negative input terminal of the differential amplifier 21. In this case, the feed back resistors 23, 24 and 25 as well as the electric source 22 for producing the reference bias voltage $V_R$ are adjusted such that the variation of the characteristic of each chemically sensitive element is corrected to obtain the optimum operating point of each chemically sensitive element. As a result, each chemically sensitive element is always maintained under its optimum operative condition in the course of measurement, thereby improving the measuring accuracy and shortening the measuring time. Thus, it is possible to fully utilize the high speed response property of the semiconductor ion sensor. Such adjustment can be effected by using a standard liquid having a known ion concentration.

The invention is not limited to the above mentioned embodiment only, but various changes and modifications may be made. For example, in the above mentioned embodiment, the ion sensor 3 is provided with three insulation gate field effect transistor elements. But, provision may be made of more than three elements. In addition, the resistance values of the reference resistors 9, 10, 11 connected to the source of each element may be made variable so as to compensate for variation of the characteristic of each element.

The chemical substance detection apparatus constructed and arranged as above described according to the invention has a number of advantages. In the first place, since each chemically sensitive element is operative by a constant current, it is possible to accurately measure the ion concentration. Secondly, each chemically sensitive element can be operated at its optimum operation point. Third, variation of characteristic of each chemically sensitive element can be compensated. Fourth, the high speed response characteristic of each chemically sensitive element can fully be displayed, thereby effecting the measurement at a high speed. Fifth, the automatic changeover of the measuring channel can be effected by an analog switch 19, thereby automating the measurement in an easy manner. Finally, use is made of a reference gate bias electric source 22 and differential amplifier 21 in common to all of measuring channels and hence the circuit is simple in construction.

What is claimed is:

1. In a chemical substance detection apparatus comprising a plurality of chemically sensitive elements constructed as an insulation gate field effect transistor formed on one or different substrates and including chemically sensitive portions selectively sensitive to different specified substances and one reference electrode, at least said chemically sensitive portions as well as said one reference electrode being adapted to detect various substances, the improvement comprising reference resistors connected to sources of said chemically sensitive elements, respectively, first amplifiers connected to said reference resistors, respectively, and supplied with the voltages produced across each of said reference resistors, said first amplifiers being operative to adjust gain thereof, a differential amplifier connected in common to said first amplifiers and having two input terminals one of which is selectively applied with the output voltage of said first amplifiers, said differential amplifier applying its output voltage to said reference electrode, and a reference gate bias voltage source connected to the other input terminal of said differential amplifier and supplying the reference gate bias voltage thereto, whereby said bias voltage applied to said reference electrode is selectively controlled such that a given electric current always flows the drain-source path of each said chemically sensitive elements to thereby selectively detect specified substances on the basis of said bias voltage value.

2. The apparatus according to claim 1, wherein said chemically sensitive element is defined by an ion sensor constructed as an insulation gate field effect transistor and including drains connected to a common electric supply source and applied with a constant direct current voltage, and source terminals and semiconductor substrates connected through reference resistors to ground.

3. The apparatus according to claim 1, wherein said chemically sensitive element is composed of an ion sensor constructed as an insulation gate field effect transistor and being selectively sensitive to three kinds of ions.

4. The apparatus according to claim 1, wherein said first amplifiers connected to said reference resistors are connected through an analog switch driven by a switching control circuit and a second amplifier to one of input terminals of said differential amplifier and between the output terminal of said second amplifier and negative input terminals of said first amplifiers is connected a feed back circuit including variable resistors.

5. A chemical substance detection apparatus comprising:
   at least one chemically sensitive element which comprises an insulation gate field effect transistor formed on a substrate and having means for chemical sensitivity to different specified substances and adapted to detect specified substances;
   a reference electrode;
   means forming reference resistance connected to the source of said at least one chemically sensitive element;
   at least one first amplifier connected to said reference resistance means and supplied with the voltage produced therefrom, said at least one first amplifier being operative to adjust gain thereof;
   a differential amplifier connected to said at least one first amplifier and having two input terminals one of which is applied with the output voltage of said at least one first amplifier, said differential amplifier applying its output voltage to said reference electrode; and
   a reference gate bias voltage source connected to the other input terminal of said differential amplifier and supplying the reference gate bias voltage thereto;
   whereby said bias voltage applied to said reference electrode is selectively controlled such that during operation a given electric current substantially always flows the drain-source path of said at least one chemically sensitive element to thereby selectively detect at least one specified substance on the basis of said bias voltage value.

6. The apparatus of claim 5 further comprising means for switching wherein the output of each of said at least one first amplifier is individually connected to said differential amplifier by said switching means so as to supply an input to said differential amplifier on a selective basis.

* * * * *